US008691853B2

(12) United States Patent
Chen et al.

(10) Patent No.: US 8,691,853 B2
(45) Date of Patent: Apr. 8, 2014

(54) METHOD OF USING DOPAMINE REUPTAKE INHIBITORS AND THEIR ANALOGS FOR TREATING AUTOIMMUNE CONDITIONS AND DELAYING OR PREVENTING AUTOIMMUNE RELATED PATHOLOGIC PROGRESSIONS

(75) Inventors: Hao Chen, Columbia, MD (US); Alexel Miagkov, Columbia, MD (US); Lisa Leary, Edgewater, MD (US); Ming Liu, Rockville, MD (US); Qi Su, Ellicott City, MD (US)

(73) Assignee: Caliper Life Sciences, Inc., Hopkinton, MA (US)

( * ) Notice: Subject to any disclaimer, the term of this patent is extended or adjusted under 35 U.S.C. 154(b) by 115 days.

(21) Appl. No.: 13/253,332

(22) Filed: Oct. 5, 2011

(65) Prior Publication Data

US 2012/0264698 A1 Oct. 18, 2012

Related U.S. Application Data

(63) Continuation-in-part of application No. 13/180,996, filed on Jul. 12, 2011, which is a continuation of application No. 12/048,334, filed on Mar. 14, 2008, now abandoned.

(60) Provisional application No. 61/389,944, filed on Oct. 5, 2010, provisional application No. 60/894,739, filed on Mar. 14, 2007.

(51) Int. Cl.
*A61K 31/4245* (2006.01)
*C07D 271/04* (2006.01)

(52) U.S. Cl.
USPC .......................................... 514/364; 548/125

(58) Field of Classification Search
None
See application file for complete search history.

(56) References Cited

U.S. PATENT DOCUMENTS

| | | | |
|---|---|---|---|
| 3,277,108 A | 10/1966 | Daeniker | |
| 4,245,100 A | 1/1981 | Kholodov et al. | |
| 4,277,609 A | 7/1981 | Stein | |
| 4,301,285 A | 11/1981 | Stein | |
| 4,371,539 A | 2/1983 | Stein | |
| 4,371,697 A | 2/1983 | Stein | |
| 4,446,322 A | 5/1984 | Stein | |
| 5,554,626 A | 9/1996 | Moldt et al. | |
| 2005/0163773 A1* | 7/2005 | Levite | 424/143.1 |
| 2005/0176680 A1 | 8/2005 | Lalji et al. | |
| 2008/0319030 A1 | 12/2008 | Chen et al. | |
| 2011/0288137 A1 | 11/2011 | Chen et al. | |

FOREIGN PATENT DOCUMENTS

| | | |
|---|---|---|
| DE | 2028880 | 12/1971 |
| GB | 1262830 | 2/1972 |

OTHER PUBLICATIONS

Blanco et al. Science 2001, 294, p. 1540-1543.*
Parshin et al. Farmakologiia i Toksikologiia, vol. 2, 1980, p. 153-158.*
R Gainetdinov et al., "Glutamatergic modulation of hyperactivity in mice lacking the dopamine transporter", PNAS, 98(20): 11047-11054 (2001).
F. Hall et al., "Sex-dependent Modulation of Ethanol Consumption in Vesicular Monoamine Transporter 2 (VMAT2) and Dopamine Transporter (DAT) Knockout Mice", Neuropsychopharmacology, 28: 620-628 (2003).
Y. Mateo et al., "Role of serotonin in cocaine effects in mice with reduced dopamine transporter function", PNAS, 101 (1): 372-377 (2004).
S. Izenwasser et al., "Differential Relationships Among Dopamine Transporter Affinities and Stimulant Potencies of Various Uptake Inhibitors", Eur. J. Pharmacol., 263: 277-83 (2004).
P. Kunko et al., "Alterations in Locomotor Activity during Chronic Cocaine Administration: Effect on Dopamine Receptors and Interaction with Opioids", J. Pharmacol. and Exp. Ther, 285(1): 277-84 (1998).
G. Campiani et al., "Synthesis and Pharmacological Evaluation of Potent and Highly Selective D3 Receptor Ligands: Inhibition of Cocaine-Seeking Behavior and the Role of Dopamine D3/D2 Receptors", J. Med. Chem., 46: 3822-3839 (2003).
F. J. Garcia-Ladona et al., "BP 897, a Selective Dopamine D3 Receptor Ligand with Therapeutic Potential for the Treatemnt of Cocaine-Addiction", CNS Drug Reviews, 9: 141-158 (2003).
S. Schlussman et al., "Locomotion, stereotype, and dopamine D1 receptors after chronic "binge" cocaine in C57BL/6J and 129/J mice", Pharmacol. Biochem. Behav., 75: 123-131 (2003).
D. Platt et al., "Suppression of cocaine- and food-maintained behavior by the D2-like receptor partial agonist terguride in squirrel monkeys", Psychopharmacology, 166: 298-305 (2003).
S. Vorel, "Dopamine D3 Receptor Antagonism Inhibits Cocaine-Seeking and Cocaine-Enhanced Brain Reward in Rats", J. Neurosci., 22(21): 9595-9603 (2002).
E. Ellinwood et al., "Effect of daily dosing duration of direct and indirect dopamine receptor agonists: cocaine cross-tolerance following chronic regimens", Eur. Neuropsychopharmacol., 12: 407-15 (2002).
J. Owens et al., "Second generation SSRIS: human monoamine transporter binding profile of escitalopram and R-fluoxetine", Encephale, 28(4): 350-5 (2002).
A. Zhang et al., "Further Studies on Conformationally Constrained Tricyclic Tropane Analogues and Their Uptake Inhibition at Monoamine Transporter Sites: Synthesis of (Z)-9-(Substituted arylmethylene)-7-azatricyclo[4.3.1.0] decanes as a Novel Class of Serotonin Transporter Inhibitors", J. Med. Chem., 45: 1930-1941 (2002).
C. Sanchez eta l., "Escitalopram, the S-(+)enantionmer of citalopram, is a selective serotonin reuptake inhibitor with potent effects in animal models predictive of antidepressant and anxiolytic activities", Psychopharmacology, 167: 353-362 (2003).

(Continued)

*Primary Examiner* — Samantha Shterengarts
*Assistant Examiner* — Ana Z Muresan
(74) *Attorney, Agent, or Firm* — Thomas H. Walls; Dann, Dorfman, Herrell and Skillman

(57) ABSTRACT

Dopamine reuptake inhibitors, and their analogs, are disclosed for treating and delaying the progression of autoimmune diseases.

15 Claims, 6 Drawing Sheets

(56) References Cited

OTHER PUBLICATIONS

Figure 1:
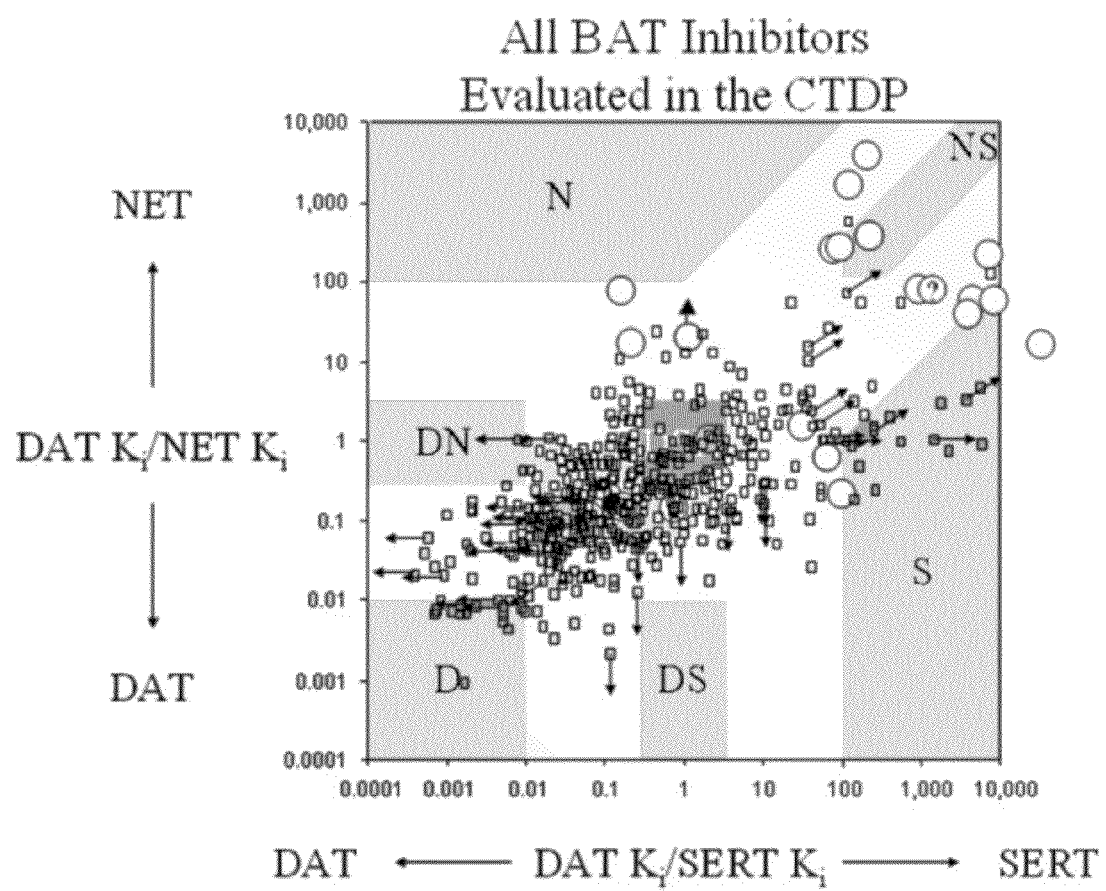
Figure 2A:
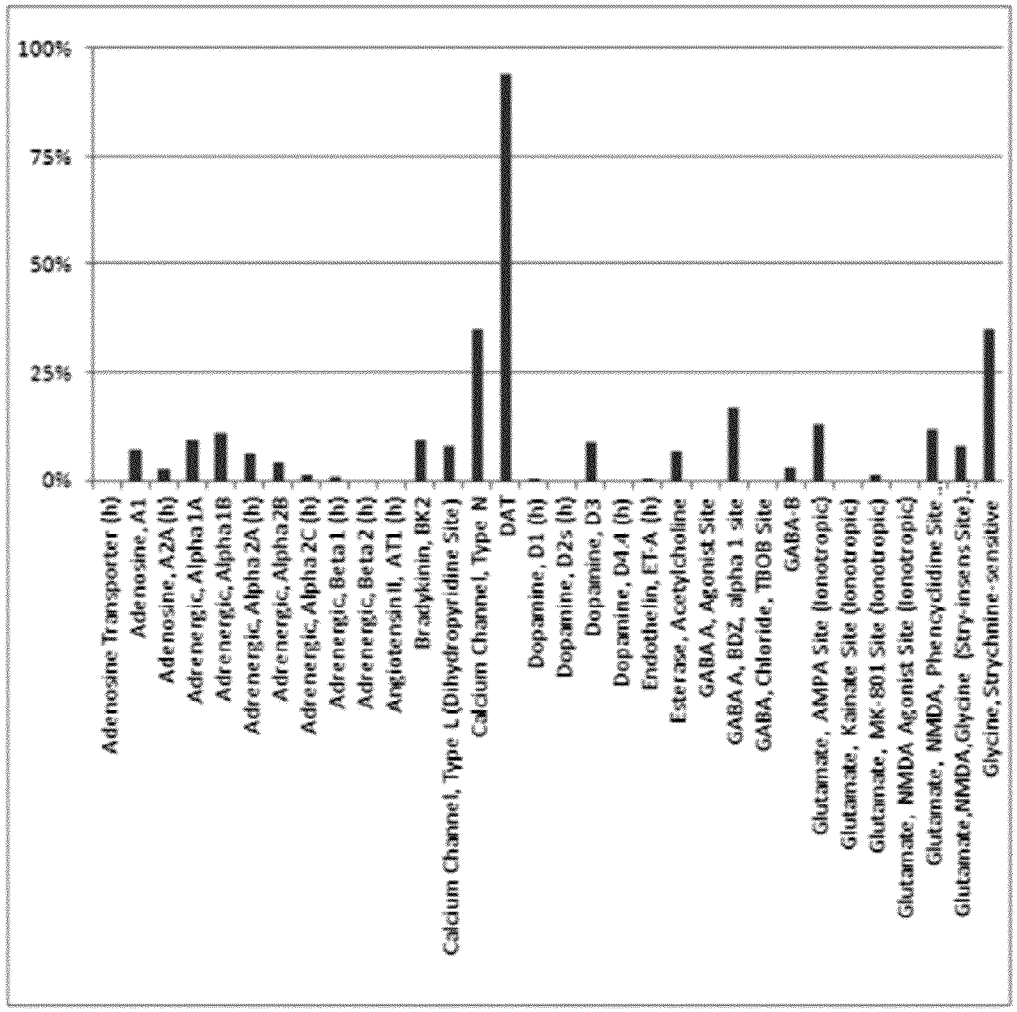
Figure 2A:
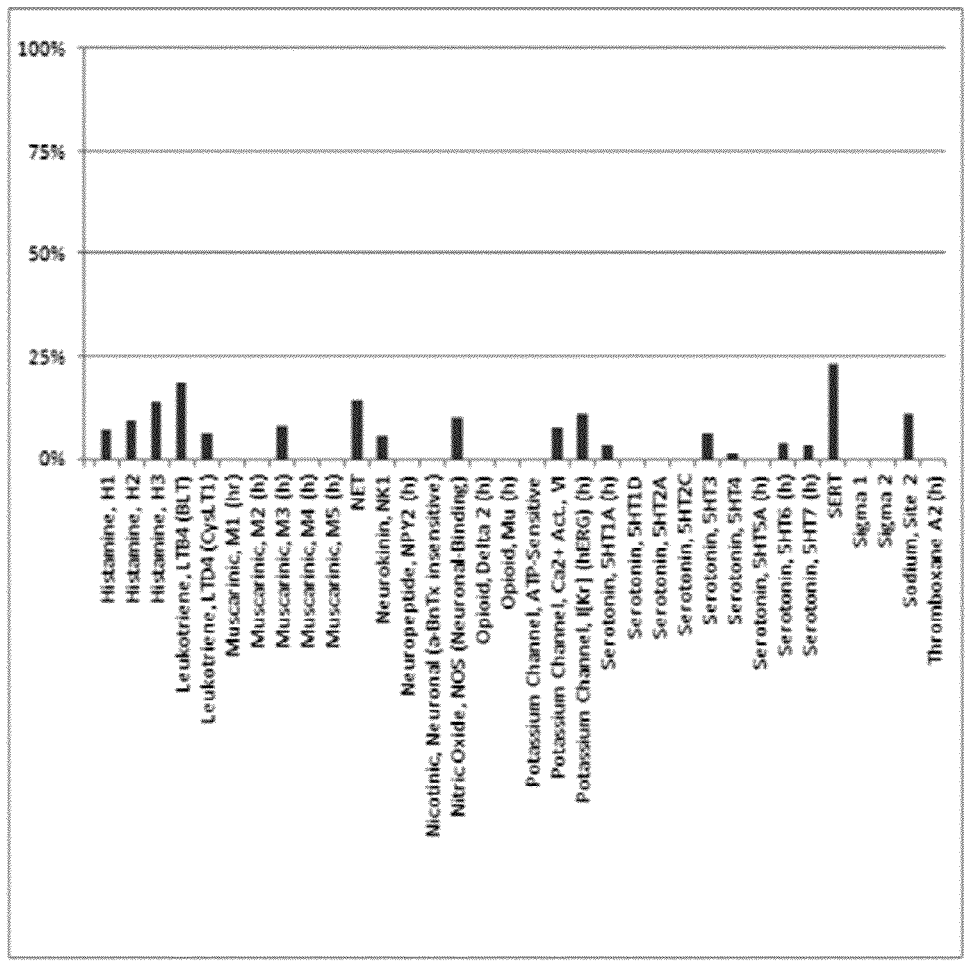
Figure 2B:
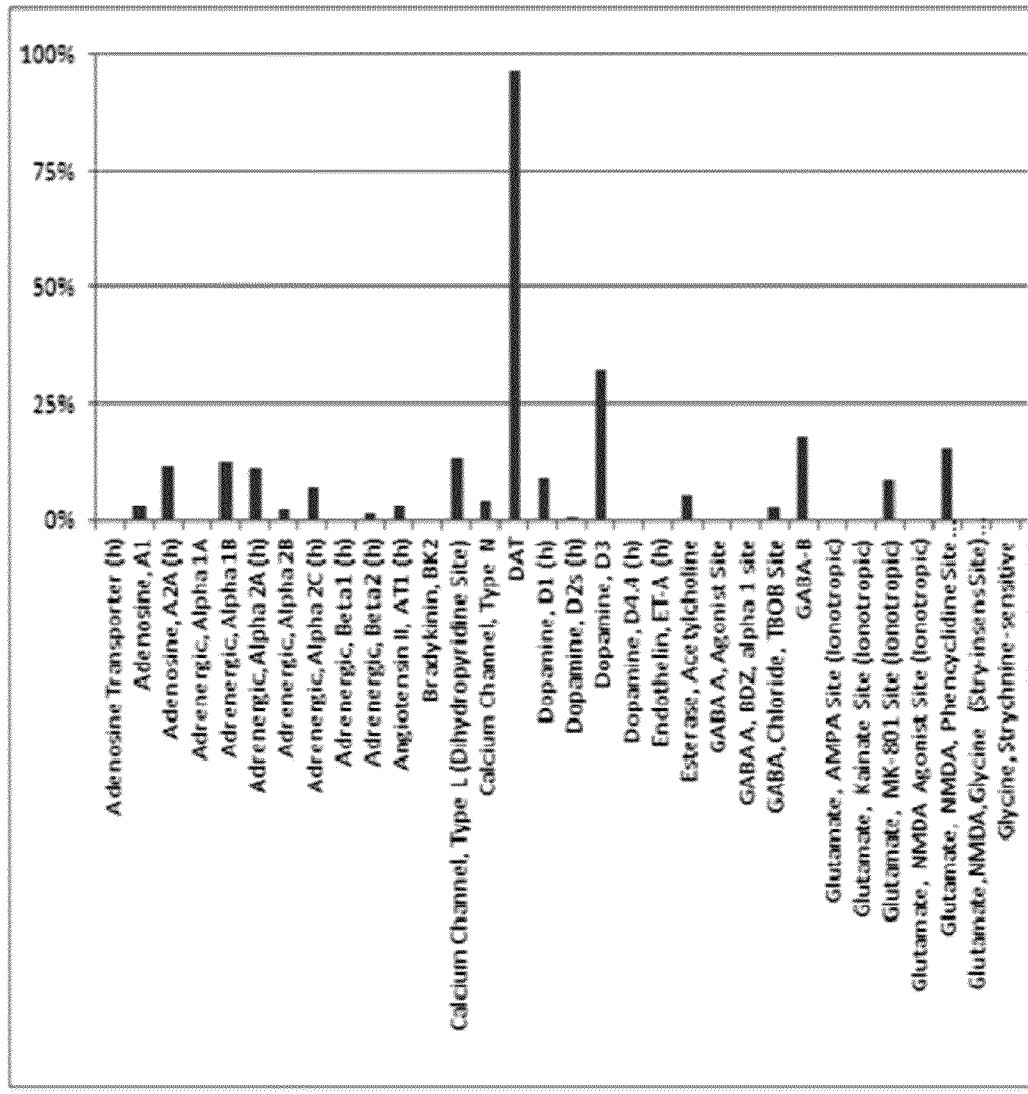
Figure 2B:
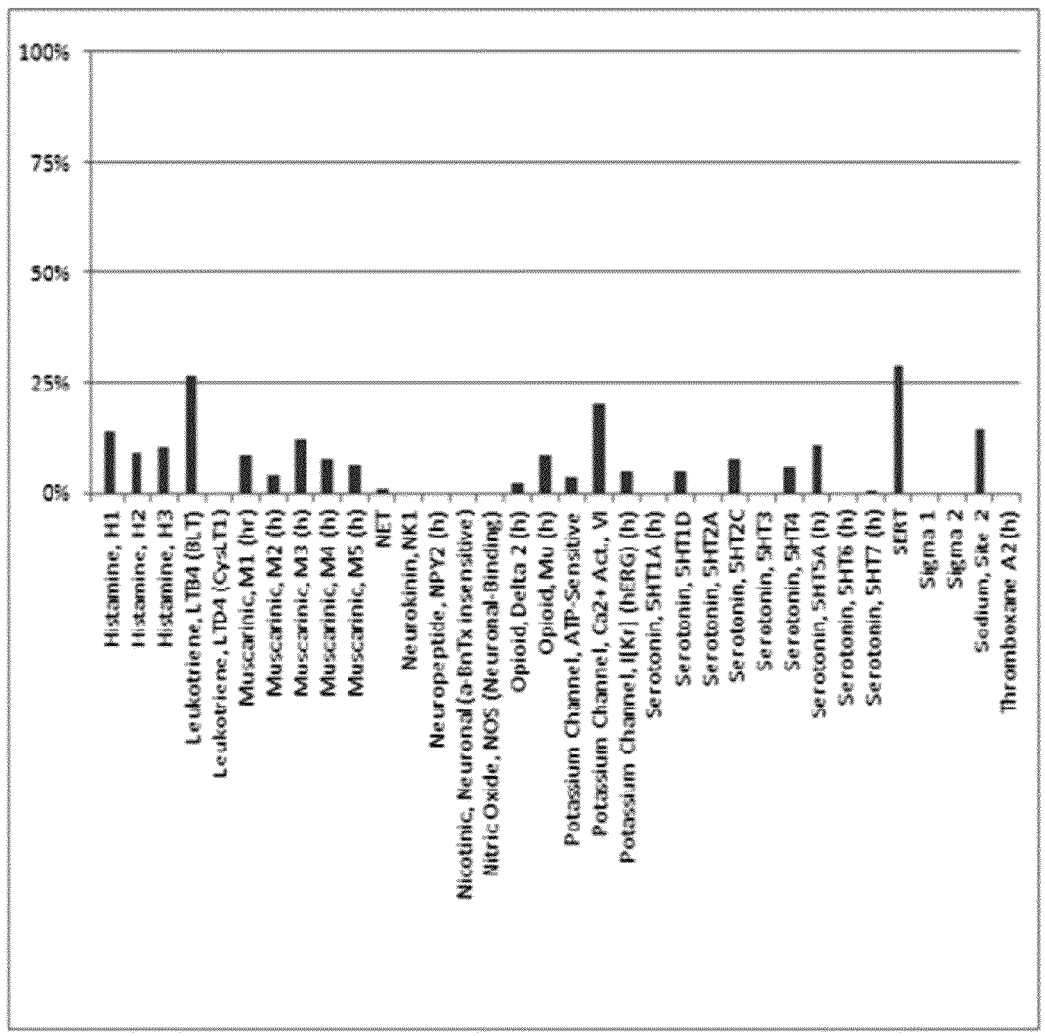

E. Fish et al., "Anxiolytic-Like Effects of Escitalopram, Citalopram, and R-Citalopram in Maternally Separated Mouse Pups", J. Pharmacol. Exp. Ther., 308: 474-80 (2004).

N. Volkow et al., "Therapeutic Doses of Oral Methylphenidate Significantly Increase Extracellular Dopamine in the Human Brain", J. Neurosci., 21(2) RC 121 (2001).

P. D'Aquila et al., "The role of dopamine in the mechanism of action of antidepressant drugs", Eur. J. Pharmacol., 405: 365-373 (2000).

I. Sora et al., "Molecular mechanisms of cocaine reward: Combined dopamine and serotonin transporter knockouts eliminate cocaine place preference", PNAS, 98(9): 5300-5305 (2001).

J. Witkin et al., "Behavorial, Toxic, and Neurochemical Effects of Sydnocarb, a Novel Psychomotor Stimulant: Comparisons with Methamphetamine", J. Pharmacol. Exp. Ther., 288(3): 1298-1310 (1999).

I.S. Slyusarenko et al., "Sydnonimines prepared from E-aminocaproic acid", Khimiya Geterotsiklicheskikh Soedinenii, 11: 1469-72 (1973) CAPLUS record.

S. Erdo et al., Inhibition of Dopamine Uptake by a New Psychostimulant Mesocarb (Sydnocarb), Polish Journal of Pharmacology and Pharmacy, 33: 141-147 (1981), Abstract.

M. Thorpy, "Therapeutic advances in narcolepsy", Sleep Medicine, 8: 427-440 (2007).

L. E. Kholodov et al., "Sydnones and sydnonimines. XXXV Salts and exocyclic derivatives of some sydnonimines", Zhurnal Organicheskoi Khimii, 3(8): 1513-1518 (1967) (CAPLUS record).

H. Takahashi et al., "The Role of Extrastriatal Dopamine D2 Receptors in Schizophrenia", Biol. Psychiatry, 59: 919-928 (2006).

L. E. Kholodov et al., "Synthesis and pharmacological activity of some 3-substituted sydnone imines", Khimiko-Farmatsevticheskii Zhurnal, 2(5): 3-7 (1968).

Z.A. Olovyanishnikova et al., "Electrophilic substitution in N-exocarbamoyl derivatives of sydnone imines", Khimiya Geterotsiklicheskikh Soedinenii, 9: 1198-203 (1975) (CAPLUS record).

Z.A. Olovyanishnikova et al., "Phenylethyl derivatives of sydnonimines", Khimiko-Farmatsevtichesii Zhurnal, 6 (6): 20-3 (1972).

Al'tshuler et al., Farmakologiya/Toksikologiya, 43: 153-158 (1980).

Definition for "acyl", Hawley's Condensed Chemical Dictionary, 14th edition (2002).

S. Izenwasser et al., "Differential relationships among dopamine transporter affinities and stimulant potencies of various uptake inhibitors", Eur. J. Pharmacol., 263: 277-283 (1994).

V.A. Krasov et al., "Sidnocarb Treatment of Young Schoolchildren with Hyperdynamic Syndrome", Zhurnal Nevropatologii I Psikhiatrii Imeni S.S. Korsakova, 88(8): 97-101 (1988).

English translation of Krasov et al., Zhurnal Nevropatologii/ Psikhiatrii Imeni S.S. Korsakova, 88(8): 97-101 (1988).

English translation of Al'tshuler et al., Farmakologiya/ Toksikologiya, 43: 153-158 (1980).

F. George, "Cocaine produces low dose locomotor depressant effects in mice", Psychopharmacology, 99: 147-150 (1989).

S.H. Heil et al., "Comparison of the subjective, physiological, and psychomotor effects of atomoxetine and methylphenidate in light drug users", Drug and Alcohol Dependence, 67: 149-156 (2002).

H. Mitchell et al., "The Effects of Norepinephrine Transporter Inactivation on Locomotor Activity in Mice", Biol. Psychiatry, 60: 1046-1052 (2006).

\* cited by examiner

METHOD OF USING DOPAMINE REUPTAKE INHIBITORS AND THEIR ANALOGS FOR TREATING AUTOIMMUNE CONDITIONS AND DELAYING OR PREVENTING AUTOIMMUNE RELATED PATHOLOGIC PROGRESSIONS

CROSS-REFERENCE TO RELATED APPLICATIONS

The present application claims the benefit of U.S. Provisional Application No. 61/389,944, filed Oct. 5, 2010. The present Application is also a Continuation-in-Part of Co-Pending application Ser. No. 13/180,996, filed Jul. 12, 2011, which is a Continuation of U.S. Non-Provisional application Ser. No. 12/048,334, filed Mar. 14, 2008, now abandoned, which claims the benefit of U.S. Provisional Patent Application No. 60/894,739, filed Mar. 14, 2007. The entire disclosures of the above-referenced applications are incorporated by reference herein.

FIELD OF INVENTION

The present invention relates to the field of pharmacological management of autoimmune diseases, such as lupus, multiple sclerosis, rheumatoid arthritis, Type 1 diabetes mellitus, psoriasis and various types of disease manifestations that are associated with activated immunocytes against host biological systems including cells, tissues and organs. More specifically, the present invention provides a method of using certain dopamine reuptake inhibitors having dopaminergic activity, alone or in combination with other therapeutic agents, for the management of the aforementioned immunological maladies generally called autoimmune diseases.

BACKGROUND OF THE INVENTION

Autoimmune diseases can be generally attributed to an over reactive immune response wherein the host immunocytes including T- and B-cells, monocytes, macrophages, and dendritic cells (DCs) are activated to attack tissues and organs of the host. These types of progressive diseases exhibit many different phenotypic manifestations. Common autoimmune diseases include lupus (systemic lupus erhythematosus or SLE), multiple sclerosis (MS), rheumatoid arthritis (RA), psoriasis and Type 1 diabetes mellitus. Less common autoimmune diseases include Ankylosing spondylitis, Crohn's disease, Graves' disease, Guillain-Barré syndrome, and Sjögren's syndrome. In all autoimmune diseases referred to hereinabove, the debilitating symptoms are a result of an overactivated host immune system assailing host cells, tissues and organs.

Lupus is a condition wherein the adaptive immune system systematically attacks the host organs including kidney, lung, liver, peripheral and central nerve system and blood vessels. It is more prevalent in women, affecting about 1.5 million Americans today.

Multiple sclerosis, known as disseminated sclerosis or encephalomyelitis disseminate, is an ailment caused by the loss of fatty myelin sheaths around the axons of the brain and spinal cord. The loss of myelin is due to attack of the host immune systems. It is also more common in women, affecting about 400,000 Americans today.

Rheumatoid arthritis is a systemic autoimmune disorder affecting 1% of the world population. The chronic illness of RA is three times more prevalent in women than men. The etiology of RA involves the host immune system assaulting the host joints.

Psoriasis is an erythemato-squamous inflammatory skin disorder which affects approximately 2 to 3% of the world population causing lifelong suffering through disfigurement and pruritus. Psoriasis is associated with various types of joint inflammation and arthritis, which can affect normal daily activities, such as use of hands, walking, sleeping, and sexual activity and lead to disability. Psoriasis is no longer regarded as a chronic primary dysregulation of keratinocyte proliferation and is now understood to be a systemic T-cell mediated autoimmune disease.

Type 1 diabetes mellitus, also known as IDDM or juvenile diabetes, affects more than 13,000 young people each year. Type 1 diabetes is a disease where the host immune system attacks the pancreatic insulin secreting beta-cells, thus rendering the host incapable of utilizing sugar.

The aforementioned progressive diseases exhibit a variety of debilitating symptoms which commonly lead to death in the absence of effective intervention and management. The management or treatment options are often limited to corticosteroids (e.g. prednisone) or chemotherapeutic agents (e.g. methotrexate, cyclophosphamide, mycophenolate). Unfortunately, the present treatment options are associated with deleterious side effects and have limited efficacy. Thus there is an urgent and unmet need for more efficacious and clinically viable agents for treating or preventing the progression of autoimmune diseases.

Dopaminergic functions may directly mediate the activities of immunocytes and by extension affect the integral mechanisms of autoimmune disease. Immunocytes, such as human peripheral blood mononuclear cells (PBMC) (Bergquist et al. 1994), neutrophils (Cosentino et al. 1999), and macrophages (Brown et al. 2003) synthesize dopamine which may be stored in vesicles. This process is similar to the storage of dopamine in neurons and other cells. Dopamine is a regulator of immunocyte activities through autocrine-paracrine mechanisms via dopaminergic receptors that are expressed on these immunocytes (Cosentino et al. 2007). There is experimental evidence indicating that dopamine may mediate immunological homeostasis and inflammatory responses by inducing apoptosis of certain immunocytes (Cioca et al. 2000; Josefsson et al. 1996).

The dopaminergic regulation of immunity may also be established via interaction between different immunocytes. The net result of these interactions can be either stimulatory or suppressive. Dendritic cells (DCs) are implicated in the synthesis, storage, release and uptake of dopamine. When these dopamine molecules are released, it may suppress the proliferation of T-cells when the DCs interact with T-cells (Saha et al. 2001). Dendritic cells have been proposed to play a pivotal role in the initiation and perpetuation of rheumatoid arthritis by presentation of arthritogenic antigens to T-cells (Nakano et al. 2009). However, it is possible that by preventing the reuptake functions of the DCs the enriched dopaminergic microenvironment may suppress T-cells and consequently attenuate the pathogenesis of rheumatoid arthritis.

Besides directly mediating immunity through autocrine-paracrine mechanisms of the immunocytes, dopamine may mediate the activities of immunocytes through neuroendocrine mechanisms. Prolactin is a pituitary hormone important for mammalian reproductive functions and milk generation. Prolactin is also a trophic factor of immunocytes (e.g. B-cells) where, prolactin produced by pituitary glands (neuroendocrine) and immunocytes (autocrine-paracrine), is needed for the maturation and proper function of immunocytes.

Dopamine inhibits prolactin production. Elevated levels of dopamine could therefore inhibit the maturation of immunocytes (e.g. B-cells) and consequently attenuate the pathogenesis of autoimmune diseases. In fact, bromocriptine, an ergoalkoid dopamine $D_2$ agonist with deleterious side effects including pleural effusions (Perez-Lloret et al. 2010), is frequently used "off-label" to manage the manifestations of lupus (Walker 2001).

Specific dopamine reuptake inhibition enhances endogenous dopaminergic activity systematically and/or within surrounding specific cellular microenvironments temporally. Such enriched dopaminergic activity may attenuate the function of immunocytes and curtail their attack against the host in autoimmune diseases. Moreover, drugs with enhanced target specificity (specific dopamine reuptake inhibitors) possess reduced promiscuity resulting in reduced side effects during treatment. Thus, an efficacious and clinically viable dopamine reuptake inhibitor may be used as a therapeutic agent for managing autoimmune diseases.

SUMMARY OF THE INVENTION

To address the need of developing more effective treatments of autoimmune diseases, the present invention provides a method employing one or more agents including dopamine reuptake inhibitors that may be used for the management of pathologic effects of autoimmune diseases.

In one aspect, the present invention provides a method of treating autoimmune disease in a patient. The method involves administering a therapeutically effective amount of at least one dopamine reuptake inhibitor. Such dopamine reuptake inhibitors may be administered individually, or in combination with at least one other therapeutic agent that is effective in autoimmune disease management. The other supplemental therapeutic agent can include at least one dopamine receptor agonist, corticosteroid, and/or chemotherapeutic agent.

Preferably, the dopamine reuptake inhibitor used in this method is 3-(phenylpropyl)-sydnonimine-N-phenylcarbamoyl, which has demonstrated the ability to attenuate the deleterious effects of autoimmune disease in an NZB-NZW F1 mouse model of lupus.

The method of the invention is expected to be effective in managing autoimmune conditions with similar underlying overtly active immunogenic mechanisms against the host. These autoimmune conditions include lupus, multiple sclerosis, psoriasis, rheumatoid arthritis, Type 1 diabetes mellitus, ankylosing spondylitis, Crohn's disease, Graves' disease, Guillain-Barré syndrome, or Sjögren's syndrome. Based on studies conducted to date by the present inventors, it appears that this invention is at least effective to attenuate manifestations of lupus.

Thus, the present invention offers an effective therapeutic approach to autoimmune management by controlling the activity of immunocytes that have been mentioned previously.

DESCRIPTION OF DRAWINGS AND TABLES

FIG. 1. A chart showing activity profiles of biogenic amine reuptake inhibitors (SERT=serotonin transporter; BAT=biogenic amine transporter; CTDP=Cocaine Therapeutic Development Program; NIDA=National Institute on Drug Abuse). The axes are ratios of inhibitory $K_i$s. The y-axis is the compound specific inhibitory potency at norepinephrine reuptake protein (NET) vs. the inhibitory potency at dopamine reuptake protein (DAT); when the ratio is 1, there is no selective inhibitory potency; when the ratio is <1, the compound are considered DAT selective. Likewise, the x-axis concerns compound selectivity between serotonin and dopamine reuptake proteins. The compounds with profiles located in the lower left-hand corner are considered to be dopamine reuptake selective. In this case, neither 3-(p-methylbenzyl)-sydnonimine-N-phenylcarbamoyl nor 3-(phenylpropyl)-sydnonimine-N-phenylcarbamoyl reside within the this chart for they do not exhibit any binding affinity with either norepinephrine or serotonin protein; 3-(phenylethyl)-sydnonimine-N-phenylcarbamoyl will reside in the very far left hand corner near the x-y origin.

FIG. 2. Graphical representation of the results of targeted screening which indicate the target specificity of representative examples of specific dopamine reuptake inhibitors (a) 3-(p-methylbenzyl)-sydnonimine-N-phenylcarbamoyl and (b) 3-(phenylpropyl)-sydnonimine-N-phenylcarbamoyl. The compounds 3-(p-methylbenzyl)-sydnonimine-N-phenylcarbamoyl and 3-(phenylpropyl)-sydnonimine-N-phenylcarbamoyl are both specific inhibitors of dopamine reuptake. A wide panel of targeted screens indicated the target specificity of 3-(p-methylbenzyl)-sydnonimine-N-phenylcarbamoyl $Ki_{DAT}$~22 nM; 3-(phenylpropyl)-sydnonimine-N-phenylcarbamoyl $Ki_{DAT}$~7.5 nM; their radioligand binding affinity towards other catecholamine reuptake sites could not be precisely determined since the $IC_{50}$s were >>100 μM. The functional radioligand reuptake inhibition determinations using rat brain synaptosomal preparations gave selectivity profiles consistent with binding data, with both compounds showing no inhibition of reuptake of norepinephrine and serotonin, but potent inhibitory dopamine reuptake activity, $EC_{50DAT}$: 3-(p-methylbenzyl)-sydnonimine-N-phenylcarbamoyl, 41 nM; 3-(phenylpropyl)-sydnonimine-N-phenylcarbamoyl, 100 nM.

FIG. 3. A graphical representation of the survival results of NZB-NZW F1 mice. NZB-NZW F1 mice develop an autoimmune disease resembling human systemic lupus erythematosus. The incidence and severity of symptoms is more pronounced in females. The lifespan for NZBWF1 females is about 245 days. As shown, treatment with 3-(phenylpropyl)-sydnonimine-N-phenylcarbamoyl extended the life expectancy of the lupus animal models.

DETAILED DESCRIPTION OF THE INVENTION

The compounds that may be used in practicing the method of this invention are specific dopamine reuptake inhibitors of the formula:

(I)

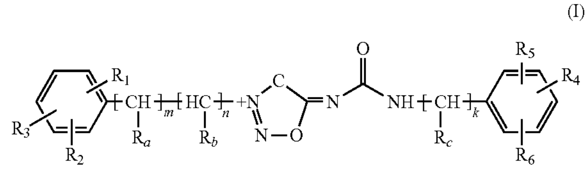

wherein $R_1$, $R_2$, $R_3$, $R_4$, $R_5$ and $R_6$, independently of one another, are substituents selected from H, $C_1$-$C_6$ alkyl, OH, halogen, $C_5$-$C_{14}$ aryl, $C_6$-$C_{20}$ aralkyl, $C_1$-$C_6$ alkylthio, $C_1$-$C_6$ alkoxy, SH, $C_2$-$C_6$ alkenyl, $C_2$-$C_6$ alkynyl, $C_3$-$C_6$ cycloalkyl, CN, $NO_2$, carboxy, carbalkoxy, carboxamido, alkylsulfonyl, alkylsulfonyloxy, aminosulfinyl, monoalkylaminosulfinyl, dialkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkyaminosulfonylalkyl, aminosulfinylalkyl, monoalkylaminosulfinylalkyl, dialkylaminosulfinylalkyl, said alkyl, alkenyl, alkynyl or cycloalkyl substituent being optionally substituted by at least one halogen, OH, SH, $NH_2$, $C_1$-$C_4$ monoalkylamino, $C_1$-$C_4$ dialkylamino, COOH, CN, $NO_2$, $C_1$-$C_4$ alkyl or $C_1$-$C_4$ alkoxy group, said aryl and aralkyl substituent being optionally substituted by at least one halogen, OH, SH, $NH_2$, $C_1$-$C_4$ monoalkylamino, $C_1$-$C_4$ dialkylamino, COOH, CN, $NO_2$, $C_1$-$C_4$ alkyl or $C_1$-$C_4$ alkoxy group;

$R_a$, $R_b$ and $R_c$, independently of one another, represent substituents selected from H, $C_1$-$C_4$ alkyl, phenyl or phenyl $C_1$-$C_4$ alkyl, said alkyl substituent, said phenyl substituent and said phenyl $C_1$-$C_4$ alkyl substituent being optionally substituted by at least one halogen, OH, SH, $NH_2$, $C_1$-$C_4$ alkylmethylamino, $C_1$-$C_4$ dialkylamino, COOH, CN, $NO_2$, $C_1$-$C_4$ alkyl or $C_1$-$C_4$ alkoxy group;

m, n and k are independent integers from 0-4, except that m+n≠0;

and the pharmaceutically acceptable salts of said compound.

It should be appreciated that compounds of Formula (I), above, may have one or more asymmetric centers and thus exist as stereoisomers, including enantiomers and diastereomers, which are usually named according to the Cahn-Ingold-Prelog system. Although the structure of Formula I is represented without regard to stereochemistry, it is intended to include all possible stereoisomers, which may be racemic mixtures or other mixtures of R and S stereoisomers (scalemic mixtures which are mixtures of unequal amounts of enantiomers), as well as resolved, substantially pure optically active forms, and pharmaceutically acceptable salts thereof.

Stereoisomers of the compounds of formula (I), above, can be selectively synthesized or separated into pure, optically-active form using conventional procedures known to those skilled in the art of organic synthesis. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

All of the various isomeric forms of the compound of Formula (I), above, are within the scope of this invention.

As used herein, the "alkyl" refers to saturated straight and branched chain hydrocarbon radicals, having 1-6 and preferably 1-4 carbon atoms. The term "alkenyl" is used to refer to unsaturated straight and branched chain hydrocarbon radicals including at least one double bond, and having 2-7 and preferably 2-5 carbon atoms. Such alkenyl radicals may be in trans (E) or cis (Z) structural configurations. The term "alkynyl" is used herein to refer to both straight and branched unsaturated hydrocarbon radicals including at least one triple bond and having 2-7 and preferably 2-5 carbon atoms.

The term "cycloalkyl" as used herein refers to a saturated cyclic hydrocarbon radical with one or more rings, having 3-14 and preferably 5 or 6-10 carbon ring-atoms.

Any alkyl, alkenyl, alkynyl or cycloalkyl moiety of a compound described herein may be substituted with one or more groups, such as halogen, OH, SH, $NH_2$, $C_1$-$C_4$ monoalkylamino, $C_1$-$C_4$ dialkylamino, COOH, CN, $NO_2$, $C_1$-$C_4$ alkyl or $C_1$-$C_4$ alkoxy.

The term "aryl" as used herein refers to an aromatic hydrocarbon radical composed of one or more rings and having 5 or 6-14 carbon atoms and preferably 5 or 6-10 carbon atoms, such as phenyl, naphtnyl, biphenyl, fluorenyl, indanyl, or the like. Any aryl moiety of a compound described herein may be substituted with one or more groups, such as halogen, OH, SH, $NH_2$, $C_1$-$C_4$ monoalkylamino, $C_1$-$C_4$ dialkylamino, COOH, CN, $NO_2$, $C_1$-$C_4$ alkyl or $C_1$-$C_4$ alkoxy. The aryl moiety is preferably substituted or unsubstituted phenyl.

The term "arylalkyl" or "aralkyl" as used herein refers to radicals having 6 to 20 carbon atoms that combine both an aryl and an alkyl group, as defined above. Any aralkyl moiety of a compound described herein may optionally be substituted with one or more of the same substituent groups mentioned above in reference to the aryl radical.

The term "halogen" or "halo" as used herein refers to Fl, Cl, Br and I.

The term "alkoxy" refers to alkyl-O—, in which alkyl is as defined above.

The term "alkylthio" refers to alkyl-S—, in which alkyl is as defined above.

The term "carboxy" refers to the moiety —C(=O)OH.

The term "carbalkoxy" refers to the moiety —C(=O)O-alkyl, in which alkyl is as defined above.

The term "carboxamido" refers to the moiety —C(=O)O—NR'R", in which R' and R", each independently represents H, alkyl, aryl or aralkyl, all as previously defined.

The term "alkylsulfonyl" refers to the moiety —S(=O)$_2$-alkyl, in which alkyl is as previously defined.

The term "alkylsulfonyloxy" refers to the moiety —OS(=O)$_2$-alkyl, wherein alkyl is as previously defined.

The term "amino(monoalkylamino-, dialkylamino-)sulfinyl" refers to the moiety —S(=O)NR'R" in which R' and R" each independently represents H, alkyl, aryl or aralkyl, all as previously defined.

The term "amino(monoalkylamino-, dialkylamino-)sulfonyl" refers to the moiety —S(=O)$_2$NR'R", in which R' and R" each independently represents H, alkyl, aryl or aralkyl, all as previously defined.

The term "alkylsulfonylamino" refers to the moiety —NHS(=O)$_2$-alkyl, in which alkyl is as previously defined.

The term "hydroxysulfonyloxy" refers to the moiety —OS(=O)$_2$OH.

The term "alkoyxsulfonyloxy" refers to the moiety —OS(=O)$_2$O-alkyl, in which alkyl is as previously defined.

The term "alkylsulfonyloxy" refers to the moiety —OS(=O)$_2$-alkyl, in which alkyl is as previously defined.

The term "hydroxysulfonyl" refers to the moiety —S(=O)$_2$OH.

The term "alkoxysulfonyl" refers to the moiety —S(=O)$_2$O-alkyl, wherein alkyl is as previously defined.

The term "alkylsulfonylalkyl" refers to the moiety -alkyl-S(=O)$_2$-alkyl, wherein alkyl (each instance) is as previously defined.

The term "amino(monoalkylamino-, dialkylamino-)sulfonylalkyl" refers to the moieties -alkyl-S(=O)$_2$—NR'R", wherein alkyl is as previously defined, and R' and R" each independently represents H, alkyl, aryl or aralkyl, all as previously defined.

The term "amino(monoalkylamino-, dialkylamino-)sulfinylalkyl" refer to the moieties -alkyl-S(=O)—NR'R", wherein alkyl is as previously defined, and R' and R" each independently represents H, alkyl, aryl or aralkyl, all as previously defined.

Preferred are the compounds of Formula (I), above, wherein phenyl rings A and/or B are mono- or di-substituted. When the A and/or B ring is mono-substituted, para-substitution is preferred. When the A and/or B ring is di-substituted, 3,4-di-substitution is preferred. Most preferred are compounds in which the A ring is para-substituted, e.g., 3-(4- methylbenzyl)sydnominine-N-phenylcarbamoyl, compounds in which the B ring is 3,4-di-substituted, e.g., 3-phenethyl-sydnominine-N-(3,4-dichlorophenyl)carbamoyl and compounds in which the A ring is para-substituted and the B ring is 3,4-di-substituted, e.g., 3-(4-nitrophenethy)-sydnominine-N-(3,4-dinitro-phenyl)carbamoyl. Also preferred are compounds wherein m+n=1 or 3 in formula (I), above.

The term "pharmaceutically acceptable salts" as used herein refers to salts derived from non-toxic physiologically compatible acids and bases, which may be either inorganic or organic. Thus, when a compound of Formula I has an acid moiety, e.g., 3-(4-carboxylbenzyl)-sydnominine-N-phenylcarbamoyl, useful salts may be formed from physiologically compatible organic and inorganic bases, including, without limitation, alkali and alkaline earth metal salts, e.g., Na, Li, K, Ca, Mg, as well as ammonium salts, and salts of organic amines, e.g., ammonium, trimethylammonium, diethylammonium, and tris-(hydroxymethyl)methylammonium salts. The compounds of the invention also form salts with organic and inorganic acids, including, without limitation, acetic, ascorbic, lactic, citric, tartaric, succinic, fumaric, maleic, malonic, mandelic, malic, phthalic, salicyclic, hydrochloric, hydrobromic, phosphoric, nitric, sulfuric, methane sulfonic, naphthalene sulfonic, benzene sulfonic, toluene sulfonic and similar known, physiologically compatible acids. In addition, when a compound of Formula I contains both a basic moiety and an acidic moiety, zwitterions ("inner salts") may be formed and are included within the term "salt(s)" as used herein.

Specific dopamine reuptake inhibitors, which are preferred compounds for use in this practice of the invention, have a dopamine transporter (DAT) binding inhibition (at 10 μm) of greater than or equal to 90% and a norepinephrine transporter protein (NET) binding inhibition (at 10 μM) of less than or equal to 20%.

In vitro studies have been performed that demonstrate the specific DAT inhibition activity of the compounds of the invention. DAT inhibition activity was tested according to the procedure described by J. Javitz et al., Mol. Pharmacol., 26: 35-44 (1984). The test results for a number of the representative compounds of the invention are reported hereinbelow.

In general, the compounds of the invention can be administered to achieve specific dopamine reuptake inhibition by using any acceptable means known in the art, either alone or in combination with one or more other therapeutic agents. Thus, the active agent(s) can be administered orally, parenterally, such as by intravenous or intraarterial infusion, intramuscular, intraperitoneal, intrathecal or subcutaneous injection, by liposome-mediated delivery, rectally, vaginally, by inhalation or insufflation, transdermally or by otic delivery.

Combination therapy may be administered using a dopamine reuptake inhibitor, as described above, and one or more dopamine receptor agonist(s), corticosteroid(s), and/or chemotherapeutic agent(s) effective for managing the manifestations of autoimmune diseases. These agents may be administered as separate dosage units or formulated for administration together, according to procedures well known to those skilled in the art. See, for example, Remington: The Science and Practice of Pharmacy, 20th ed., A. Genaro et al., Lippencot, Williams & Wilkins, Baltimore, Md. (2000). The combinations administered in accordance with this invention include combinations of two or more of the dopamine reuptake inhibitors described above, or one or more such inhibitors in conjunction with at least one dopamine receptor agonist, corticosteroid and chemotherapeutic agent.

The dopamine receptor agonist that may be used in accordance with the present invention includes, without limitation, cabergoline, pergolide, pramipexole, ropinirole, apomorphine, rotigotine, fenoldopam, dopamine, and levodopa. These are clinically effective dopamine receptor agonists, which should be administered in accordance with the manufacturers' recommendations.

The dopamine reuptake inhibitor(s) described above may be co-administered with a corticosteroid including, without limitation, prednisone, betamethasone, dexamethasone, hydrocortisone, and methylprednisone acetate, or a combination thereof.

The dopamine reuptake inhibitor(s) described above may also be co-administered with a chemotherapeutic agent, including, without limitation, methotrexate, cyclophosphamide, mycophenolate, chlorambucil, azathioprine, 6-mercaptopurine, leflunomide, cyclosporine, tacrolimus, and sirilimus, or a combination thereof.

Normally, a daily dose of the compound of the invention in the range from about 0.01 mg to about 200 mg/kg of body weight can be administered. A daily dose of from 0.1 to 100, and preferably from 1 to 30 mg/kg per day in one or more applications per day should be effective to produce the desired result. By way of example, a suitable dose for oral administration would be in the range of 1-30 mg/kg of body weight per day, whereas a typical dose for intravenous administration would be in the range of 1-10 mg/kg of body weight per day. Of course, as those skilled in the art will appreciate, the dosage actually administered will depend upon the condition being treated, the age, health and weight of the recipient, the type of concurrent treatment, if any, and the frequency of treatment. Moreover, the effective dosage amount may be determined by one skilled in the art on the basis of routine empirical activity testing to measure the bioactivity of the compound(s) in a bioassay, and thus establish the appropriate dosage to be administered.

As used herein, the expression "method of treating autoimmune disease" refers to a treatment using one or more of the compounds described herein which provide(s) relief from or alleviation of symptoms of the disease, delays onset or progression of the disease or effects a complete cure of the disease. The autoimmune diseases include, without limitation, lupus, Type I diabetes mellitus, multiple sclerosis, rheumatoid arthritis, ankylosing spondylitis, Crohn's disease, Graves' disease, Guillain-Barré syndrome, psoriasis and Sjögren's syndrome. The method of treating autoimmune symptoms and delaying or preventing autoimmune associated pathologic conditions, such as lupus, multiple sclerosis, and rheumatoid arthritis with dopamine reuptake inhibitors described herein may be used as an adjunct to the current standards of care.

The compounds of the invention will typically be administered from 1-4 times a day, so as to deliver the above-mentioned daily dosage. However, the exact regimen for administration of the compounds and compositions described herein will necessarily be dependent on the needs of the individual subject being treated, the type of treatment administered and the judgment of the attending medical specialist. As used herein, the term "subject" includes both humans and animals.

The compounds of the invention may be administered as such, or in a form from which the active agent can be derived, such as a prodrug. A prodrug is a derivative of a compound described herein, the pharmacologic action of which results from the conversion by chemical or metabolic processes in vivo to the active compound. Prodrugs include, without limitation, ester derivatives of the compounds of formula I, above.

Other prodrugs may be prepared according to procedures well known in the field of medicinal chemistry and pharmaceutical formulation science. See, e.g., Lombaert et al., J. Med. Chem., 37: 498-511 (1994); and Vepsalainen, Tet. Letters, 40: 8491-8493 (1999).

The DAT specific compounds described herein and the pharmaceutically acceptable salts thereof are preferably formulated in unit dosage form for ease of administration and uniformity of dosage. The expression "unit dosage form" as used herein refers to a physically discrete unit of the active agent appropriate for the subject to be treated. Each dose should contain the quantity of active ingredient calculated to produce the desired therapeutic effect, either as such, or in association with the selected pharmaceutical carrier medium and/or supplemental active agent(s), if any. Typically, the DAT inhibitory compounds of the invention will be administered in dosage form containing from about 0.01 mg to about 200 mg of the active ingredient per kilogram of the subject weight, with a range of about 5 mg to about 15 mg per kilogram of subject weight being preferred.

The orally administered dosage unit may be in the form of tablets, caplets, dragees, pills, semisolids, soft or hard gelatin capsules, aqueous or oily solutions, emulsions, suspensions or syrups. Suitable dosage forms for parenteral administration include injectable solutions or suspensions, suppositories, powder formulations, such as microcrystals or aerosol spray. The active agent may also be incorporated into a conventional transdermal delivery system.

As used herein, the expression "pharmaceutically acceptable carrier medium" includes any and all solvents, diluents, or other liquid vehicle, dispersion or suspension aids, surface agent agents, isotonic agents, thickening or emulsifying agents, preservatives, solid binders, lubricants, fillers and the like as suited for the particular dosage form desired. Remington: The Science and Practice of Pharmacy, 20$^{th}$ edition, A. R. Genaro et al., Part 5, Pharmaceutical Manufacturing, pp. 669-1015 (Lippincott Williams & Wilkins, Baltimore, Md./Philadelphia, Pa.) (2000)) discloses various carriers used in formulating pharmaceutical compositions and known techniques for the preparation thereof. Except insofar as any conventional pharmaceutical carrier medium is incompatible with the DAT inhibitor compounds of the present invention, such as by producing an undesirable biological effect or otherwise interacting in an deleterious manner with any other component(s) of a formulation comprising such compounds, its use is contemplated to be within the scope of this invention.

For the production of solid dosage forms, including hard and soft capsules, the therapeutic agent may be mixed with pharmaceutically inert, inorganic or organic excipients, such as lactose, sucrose, glucose, gelatine, malt, silica gel, starch or derivatives thereof, talc, stearic acid or its salts, dried skim milk, vegetable, petroleum, animal or synthetic oils, wax, fat, polyols, and the like. For the production of liquid solutions, emulsions or suspensions or syrups one may use excipients such as water, alcohols, aqueous saline, aqueous dextrose, polyols, glycerine, lipids, phospholipids, cyclodextrins, vegetable, petroleum, animal or synthetic oils. For suppositories one may use excipients, such as vegetable, petroleum, animal or synthetic oils, wax, fat and polyols. For aerosol formulations, one may use compressed gases suitable for this purpose, such as oxygen, nitrogen and carbon dioxide. The pharmaceutical composition or formulation may also contain one or more additives including, without limitation, preservatives, stabilizers, e.g., UV stabilizers, emulsifiers, sweeteners, salts to adjust the osmotic pressure, buffers, coating materials and antioxidants.

The present invention further provides controlled-release, sustained-release, or extended-release therapeutic dosage forms for the pharmaceutical composition, in which the composition is incorporated into a delivery system. This dosage form controls release of the active agent(s) in such a manner that an effective concentration of the active agent(s) in the bloodstream can be maintained over an extended period of time, with the concentration in the blood remaining relatively constant, to improve therapeutic results and/or minimize side effects. Additionally, a controlled-release system would provide minimum peak to trough fluctuations in blood plasma levels of the active agent.

In the pharmaceutical compositions of the invention, the active agent(s) may be present in an amount of at least 0.5 and generally not more than 95% by weight, based on the total weight of the composition, including carrier medium and/or supplemental active agent(s), if any. Preferably, the proportion of active agent(s) varies between 30-90% by weight of the composition.

The synthesis, formulation of pharmaceutical compositions, preparation of suitable dose forms, mode and amounts of administration of such dopamine reuptake inhibitors are described in detail in U.S. Patent Application Publication No. US 2009/0215839.

One compound that has been tested for use in the method of the invention is 3-(phenylpropyl)-sydnonimine-N-phenylcarbamoyl. Additional compounds that are also dopamine reuptake inhibitors and may be utilized in the present method include, without limitation: 3-(3,5-difluorobenzyl)-sydnonimine-N-phenylcarbamoyl, 3-(3-fluorobenzyl)-sydnonimine-N-phenylcarbamoyl, 3-(4-trifluoromethyl-benzyl)-sydnonimine-N-phenylcarbamoyl, 3-(4-fluorobenzyl)-sydnonimine-N-phenylcarbamoyl, 3-(4-tert-butylbenzyl)-sydnonimine-N-phenylcarbamoyl, 3-(4-methylbenzy)-sydnonimine-N-(4-trifluoromethyl-phenyl)carbamoyl, 3-(4-methylbenzyl)-sydnonimine-N-phenylcarbamoyl, 3-(4-nitrophenethyl)-sydnonimine-N-(3,4-dinitrophenyl) carbamoyl and 3-(4-methylbenzyl)-sydnonimine-N-(4-dimethylamino-phenyl)carbamoyl.

FIG. 1 shows the activity profiles of biogenic amine reuptake inhibitors that have been discovered and tested by the National Institute on Drug Abuse (NIDA). The compounds with profiles located in the lower left-hand corner are considered to be dopamine reuptake selective, yet none of them is specific for dopamine reuptake inhibition. Indeed, all display some NET inhibitory activity. This distribution is based on the results of certain binding assays which are described below.

As shown in FIG. 2, a wide panel of targeted screens indicated the target specificity of 3-(4-methylbenzyl)-sydnonimine-N-phenylcarbamoyl (FIG. 2(*a*)) and 3-(phenylpropyl)-sydnonimine-N-phenylcarbamoyl (FIG. 2(*b*)) at 10 μM. The experiments referred to herein are described in detail in U.S. Patent Application Publication No. US 2009/0215839.

The methods of the present invention will normally include medical follow-up to determine the therapeutic or prophylactic effect brought about in the patient undergoing treatment with the compound(s) and/or composition(s) described herein.

The following examples are provided to describe the invention in further detail. These examples are provided for illustrative purposes only and are not intended to limit the invention in any way.

EXAMPLE 1

When evaluated in the radioligand binding assays, compounds were tested at 10 μM. At this specific concentration, compounds showed ≥90% inhibitory effect in the DAT binding assay (radioligand $^3$H-WIN5428) and <20% inhibition in the NET binding assay (radioligand $^3$H-Nisoxetine) are considered to be DAT specific. For instance, 3-(p-methylbenzyl)-sydnonimine-N-phenylcarbamoyl at 10 µM showed 94% inhibitory effect in the DAT binding assay; 14% in NET; 3-(p-methylbenzyl)-sydnonimine-N-phenylcarbamoyl was considered to be DAT specific. 3-(phenylpropyl)-sydnonimine-N-phenylcarbamoyl at the same concentration showed inhibitory effect with DAT about 96%; with NET, 1%. Likewise, 3-(phenylpropyl)-sydnonimine-N-phenylcarbamoyl was considered to be an DAT specific inhibitor. 3-(phenylethyl)-sydnonimine-N-phenylcarbamoyl, on the other hand, showed an inhibitory effect at DAT about 100% but with NET, 35% (at 10 µM), thus, 3-(phenylethyl)-sydnonimine-N-phenylcarbamoyl was considered to be a selective (instead of specific) DAT inhibitor.

EXAMPLE 2

Specific binding affinities in combination with functional radioligand uptake assays confirmed the selection threshold. 3-(p-methylbenzyl)-sydnonimine-N-phenylcarbamoyl showed a specific affinity with DAT $Ki_{DAT}$~22 nM; 3-(phenylpropyl)-sydnonimine-N-phenylcarbamoyl, $Ki_{DAT}$~7.5 nM; their radioligand binding affinity towards other catecholamine reuptake sites could not be precisely determined since the $IC_{50}$s were >100 µM. The functional radioligand reuptake inhibition determinations using rat brain synaptosomal preparations gave selectivity profiles consistent with binding data, with both compounds showing no inhibition of reuptake of norepinephrine and serotonin, but potent inhibitory DA reuptake activity ($EC_{50DAT}$: 3-(p-methylbenzyl)-sydnonimine-N-phenylcarbamoyl, 41 nM; 3-(phenylpropyl)-sydnonimine-N-phenylcarbamoyl, 100 nM). The corresponding data for 3-(phenylethyl)-sydnonimine-N-phenylcarbamoyl are binding, $Ki_{DAT}$=15 nM, $Ki_{NET}$>>10 µM; and functional, $EC_{50DAT}$=100 nM, $EC_{50NET}$=4.4 µM indicating DAT selectivity). One of the most important safety issues concerning treating complex disease conditions is potential drug-drug interactions. All three compounds showed no apparent activity against the most prevalent human cytochrome P450 enzymes (CYP1A1, CYP2A6, CYP2C19, CYP2C9, CYP2D6 and CYP3A4).

EXAMPLE 3

Mediation of lupus conditions: Systemic lupus erythematosus (SLE) is a chronic, inflammatory, autoimmune disease of unknown origin. NZBWF1/J (or NZB/W/J or NZB-NZW F1) develops an autoimmune disease resembling human systemic lupus erythematosus. Autoimmunity is characterized by high levels of antinuclear antibodies, hemolytic anemia, proteinuria, and progressive immune complex glomerulonephritis (GN). The incidence and severity of symptoms are more pronounced in females (Rudofsky and Lawrence, 1999). The penetrance for murine glomerulonephritis (GN) is about 85 (Morel and Wakeland, 1998) and the average lifespan for females NZBWF1 is 245 days. NZBWF1/J mice have been used as a model for autoimmune disease since the early 1960s.

Figure 3:
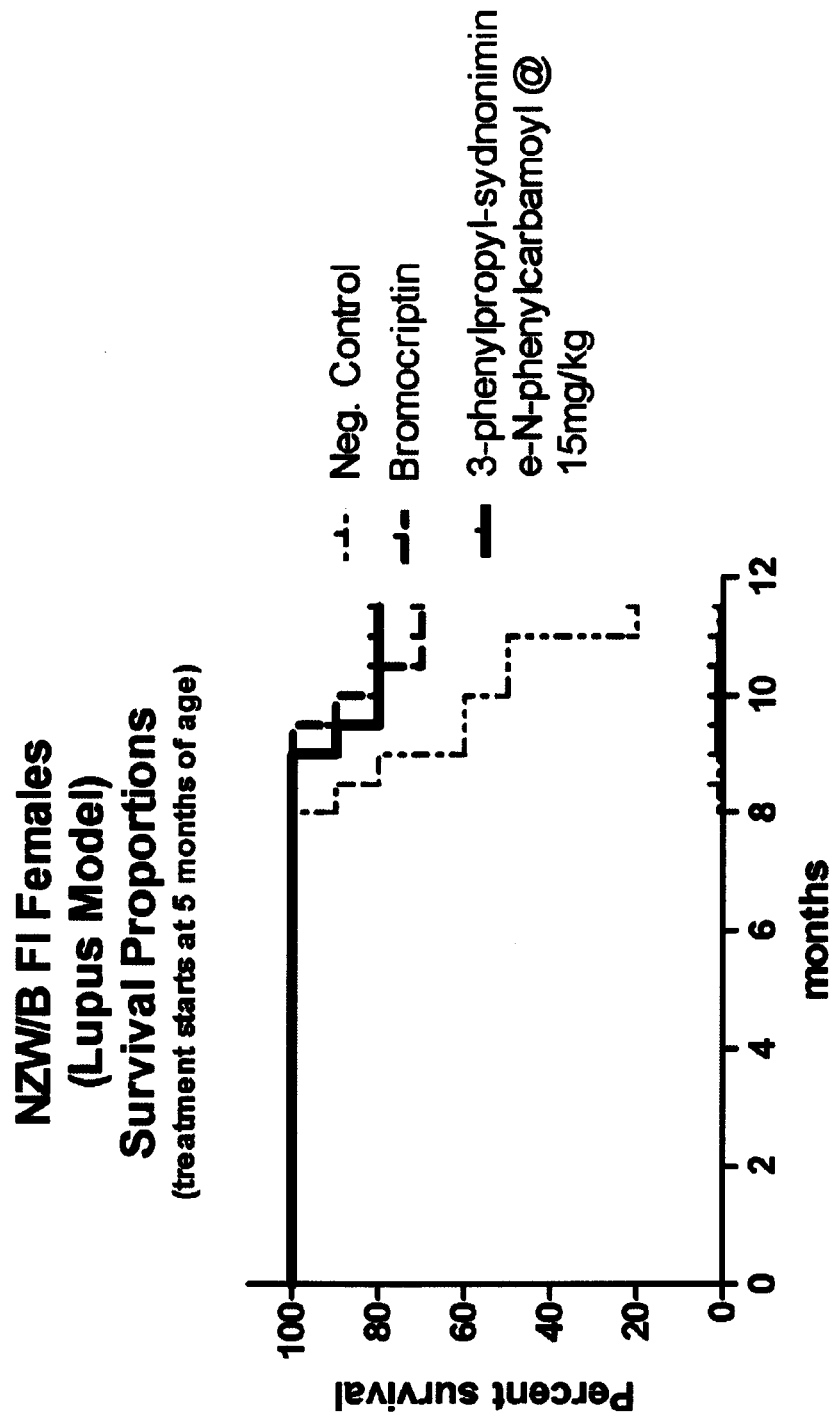

NZBWF1/J mice were used in this study. 40 NZBWF1/J mice (Jax labs; date of birth Oct. 13, 2009) were randomly divided into 4 groups (10 in each group). These animals were housed in groups (n=5) and kept under a 12-hr light/dark cycle with food and water available ad libitum for approximately 5 months. Starting at or about the end of the 5$^{th}$ month, different groups of mice were then treated either with a drug, bromocriptine, known to attenuate the effects of lupus (positive control) at 2.5 mg/kg; or with vehicles (aqueous mixture of neutral solvents) as negative control (un-treated); or with 3-(phenylpropyl)-sydnonimine-N-phenylcarbamoyl (dopamine reuptake inhibitor) at either 5 mg/kg and 15 mg/kg. After 7 months, 80% of the vehicle treated (untreated) subjects died, whereas 70% (@5 mg/kg) and 80% (@15 mg/kg) of the dopamine reuptake inhibitor treated mice survived healthily. After 7 months, 70% of the mice in the positive control group, treated with bromocriptin (@2.5 mg/kg) survived healthily. The result of this study is shown in Table 1 and FIG. 3.

This study confirms that in an animal model of lupus, the specific dopamine reuptake inhibitor, 3-(phenylpropyl)-sydnonimine-N-phenylcarbamoyl, is at least comparable and possibly more clinically viable than bromocriptine. Indeed, the dopamine reuptake inhibitor tested prolonged the healthy life of NZBWF15 mice after the onset of the autoimmune disease in the model.

TABLE 1

NZB-NZW F1 (Lupus Model) Percent Survival Data

| | Percent Survival of Subjects | | | |
|---|---|---|---|---|
| Months | Neg. Control Vehicle Treated | Bromocriptin (2.5 mg/kg) | 3-(phenylpropyl)-sydnonimine-N-phenylcarbamoyl (5 mg/kg) | 3-(phenylpropyl)-sydnonimine-N-phenylcarbamoyl (15 mg/kg) |
| 0.0 | 100 | 100 | 100 | 100 |
| 8.0 | 90 | 100 | 100 | 100 |
| 8.5 | 80 | 100 | 100 | 100 |
| 9.0 | 60 | 100 | 100 | 90 |
| 9.5 | 60 | 90 | 90 | 80 |
| 10.0 | 50 | 80 | 80 | 80 |
| 10.5 | 50 | 70 | 80 | 80 |
| 11.0 | 20 | 70 | 70 | 80 |
| 11.5 | 20 | 70 | 70 | 80 |

Log-Rank (Mantel-Cox) Test

| | |
|---|---|
| Chi Square | 9.54 |
| df | 3 |
| P-Value | 0.0229 |
| Are the survival curves significantly different? | Yes |

Log-Rank Test for Trend

| | |
|---|---|
| Chi Square | 6.043 |
| df | 1 |
| P-Value | 0.014 |
| Significant Trend? | Yes |

The foregoing specification includes citations to certain patent and literature references, which are provided to indicate the state of the art to which this invention pertains. The entire disclosure of each of the cited references is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope of the appended claims. Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compositions and methods of use thereof that embody the present invention can, in alternate embodiments, be more specifically defined by any of the transitional terms "comprising", "consisting essentially of" and "consisting of".

REFERENCES

Bergquist J, Tarkowski A, Ekman R, Ewing A. Discovery of endogenous catecholamines in lymphocytes and evidence for catecholamine regulation of lymphocyte function via an autocrine loop. Proc Natl Acad Sci USA. Dec. 20, 1994; (26):12912-6.
Brown S W, Meyers R T, Brennan K M, Rumble J M, Narasimhachari N, Perozzi E F, Ryan J J, Stewart J K, Fischer-Stenger K. Catecholamines in a macrophage cell line. J Neuroimmunol. 2003 February; 135(1-2):47-55.
Cioca D P, Watanabe N, Isobe M. Apoptosis of peripheral blood lymphocytes is induced by catecholamines. Jpn Heart J. 2000 May; 41(3):385-98.
Cosentino M, Marino F, Bombelli R, Ferrari M, Lecchini S, Frigo G. Endogenous catecholamine synthesis, metabolism, storage and uptake in human neutrophils. Life Sci. 1999; 64(11):975-81.
Cosentino M, Fietta A M, Ferrari M, Rasini E, Bombelli R, Carcano E, Saporiti F, Meloni F, Marino F, Lecchini S. Human CD4+CD25+ regulatory T cells selectively express tyrosine hydroxylase and contain endogenous catecholamines subserving an autocrine/paracrine inhibitory functional loop. Blood. Jan. 15, 2007; 109(2):632-42. Epub Sep. 19, 2006.
Josefsson E, Bergquist J, Ekman R, Tarkowski A. Catecholamines are synthesized by mouse lymphocytes and regulate function of these cells by induction of apoptosis. Immunology. 1996 May; 88(1):140-6.
Morel L, Wakeland E K. Susceptibility to lupus nephritis in the NZB/W model system. Curr Opin Immunol. 1998 December; 10(6):718-25.
Nakano K, Matsushita S, Saito K, Yamaoka K, Tanaka Y. Dopamine as an immune-modulator between dendritic cells and T cells and the role of dopamine in the pathogenesis of rheumatoid arthritis. Nihon Rinsho Meneki Gakkai Kaishi. 2009 February; 32(1):1-6.
Perez-Lloret S, Bondon-Guitton E, Rascol O, Montastruc J L; and the French Association of Regional Pharmacovigilance Centers. Adverse drug reactions to dopamine agonists: A comparative study in the french pharmacovigilance database. Mov Disord. Sep. 15, 2010; 25(12):1876-80.
Rudofsky U H, Lawrence D A. New Zealand mixed mice: a genetic systemic lupus erythematosus model for assessing environmental effects. Environ Health Perspect. 1999 October; 107 Suppl 5:713-21.
Saha B, Mondal A C, Majumder J, Basu S, Dasgupta P S. Physiological concentrations of dopamine inhibit the proliferation and cytotoxicity of human CD4+ and CD8+ T cells in vitro: a receptor-mediated mechanism. Neuroimmunomodulation. 2001; 9(1):23-33.
Walker S E. Modulation of hormones in the treatment of lupus. Am J Manag Care. 2001 October; 7(16 Suppl): S486-9.

We claim:

1. A method of providing relief from or alleviating symptoms of or delaying the progression of lupus in a patient in need of said provision of relief or alleviation of symptoms or delay of progression, the method comprising administering a therapeutically effective amount of at least one compound having the formula:

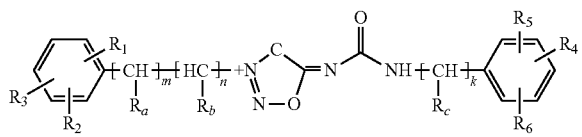

wherein $R_1$, $R_2$, $R_3$, $R_4$, $R_5$ and $R_6$, independently of one another, are substituents selected from H, $C_1$-$C_6$ alkyl, OH, halogen, $C_5$-$C_{14}$ aryl, $C_6$-$C_{20}$ aralkyl, $C_1$-$C_6$ alkylthio, $C_1$-$C_6$ alkoxy, SH, $C_2$-$C_6$ alkenyl, $C_2$-$C_6$ alkynyl, $C_3$-$C_6$ cycloalkyl, CN, $NO_2$, carboxy, carbalkoxy, carboxamido, alkylsulfonyl, alkylsulfonyloxy, aminosulfinyl, monoalkylaminosulfinyl, dialkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkyaminosulfonylalkyl, aminosulfinylalkyl, monoalkylaminosulfinylalkyl, dialkylaminosulfinylalkyl, said alkyl, alkenyl, alkynyl or cycloalkyl substituent being optionally substituted by at least one halogen, OH, SH, $NH_2$, $C_1$-$C_4$ monoalkylamino, $C_1$-$C_4$ dialkylamino, COOH, CN, $NO_2$, $C_1$-$C_4$ alkyl or $C_1$-$C_4$ alkoxy group, said aryl and aralkyl substituent being optionally substituted by at least one halogen, OH, SH, $NH_2$, $C_1$-$C_4$ monoalkylamino, $C_1$-$C_4$ dialkylamino, COOH, CN, $NO_2$, $C_1$-$C_4$ alkyl or $C_1$-$C_4$ alkoxy group;
$R_a$, $R_b$ and $R_c$, independently of one another, represent substituents selected from H, $C_1$-$C_4$ alkyl, phenyl or phenyl $C_1$-$C_4$ alkyl, said alkyl substituent, said phenyl substituent and said phenyl $C_1$-$C_4$ alkyl substituent being optionally substituted by at least one halogen, OH, SH, $NH_2$, $C_1$-$C_4$ alkylmethylamino, $C_1$-$C_4$ dialkylamino, COOH, CN, $NO_2$, $C_1$-$C_4$ alkyl or $C_1$-$C_4$ alkoxy group;
m, n and k are independent integers from 0-4, except that m+n≠0;
and the pharmaceutically acceptable salts of said compound.

2. The method according to claim 1, wherein said at least one compound administered is selected from the group consisting of
3-(phenylpropyl)-sydnonimine-N-phenylcarbamoyl,
3-(3,5-difluorobenzyl)-sydnonimine-N-phenylcarbamoyl,
3-(3-fluorobenzyl)-sydnonimine-N-phenylcarbamoyl,
3-(4-trifluoromethyl-benzyl)-sydnonimine-N-phenylcarbamoyl,
3-(4-fluorobenzyl)-sydnonimine-N-phenylcarbamoyl,
3-(4-tert-butylbenzyl)-sydnonimine-N-phenylcarbamoyl,
3-(4-methylbenzyl)-sydnonimine-N-(4-trifluoromethylphenyl)carbamoyl,
3-(4-methylbenzyl)-sydnonimine-N-phenylcarbamoyl, 3-(4-nitrophenethyl)-sydnonimine-N-(3,4-dinitrophenyl)carbamoyl and 3-(4-methylbenzyl)-sydnonimine-N-(4-dimethylaminophenyl)carbamoyl.

3. The method according to claim 1, wherein said at least one compound administered is 3-(phenylpropyl)-sydnonimine-N-phenylcarbamoyl.

4. The method according to claim 1, wherein said at least one compound is administered in conjunction with at least one other therapeutic agent selected from the group consisting of a dopamine receptor agonist, corticosteroid, and chemotherapeutic agent.

5. The method according to claim 4, wherein said compound is administered in conjunction with a dopamine receptor agonist selected from the group consisting of cabergoline, pergolide, pramipexole, ropinirole, apomorphine, rotigotine, fenoldopam, dopamine and levodopa.

6. The method according to claim 4, wherein said compound is administered in conjunction with a corticosteroid selected from the group consisting of betamethasone, dexamethasone, hydrocortisone, methyl prednisone acetate, and prednisone.

7. The method according to claim 4, wherein said compound is administered in conjunction with a chemotherapeutic agent selected from the group consisting of cyclophosphamide, chlorambucil, azathioprine, methotrexate, 6-mercaptopurine, leflunomide, cyclosporine, tacrolimus, sirilimus, and mycophenolate.

8. The method according to claim 1, wherein said at least one compound is administered in solid form, also comprising a pharmaceutically acceptable excipient.

9. The method according to claim 1, wherein said at least one compound is administered in liquid form, also comprising a pharmaceutically acceptable diluents.

10. The method according to claim 1, wherein said at least one compound is administered in dosage unit form.

11. The method according to claim 10, wherein said compound is administered in dosage unit form containing from about 0.01 to about 200 mg of said compound per kilogram of patient body weight per day.

12. The method according to claim 11, wherein said dosage unit includes a pharmaceutically acceptable vehicle.

13. The method according to claim 11, wherein said dosage unit includes a pharmaceutically suitable vehicle for extended release.

14. The method according to claim 1, wherein said compound is administered via a route selected from the group consisting of orally, parenterally, by intraperitoneal injection, by intrathecal injection, by subcutaneous injection, and transdermally.

15. The method according to claim 1, wherein said at least one compound is administered as a prodrug.

* * * * *